United States Patent
Ettlin (10) Patent No.: US 11,040,143 B2
(45) Date of Patent: Jun. 22, 2021

(54) DISCHARGER WITH IMPROVED PIERCING TIP

(71) Applicant: Sulzer Mixpac AG, Haag (CH)

(72) Inventor: Josef Ettlin, Eichberg (CH)

(73) Assignee: SULZER MIXPAC AG, Haag (CH)

(*) Notice: Subject to any disclaimer, the term of this patent is extended or adjusted under 35 U.S.C. 154(b) by 652 days.

(21) Appl. No.: 15/755,838

(22) PCT Filed: Aug. 19, 2016

(86) PCT No.: PCT/EP2016/069720
§ 371 (c)(1),
(2) Date: Feb. 27, 2018

(87) PCT Pub. No.: WO2017/036823
PCT Pub. Date: Mar. 9, 2017

(65) Prior Publication Data
US 2018/0326154 A1 Nov. 15, 2018

(30) Foreign Application Priority Data
Aug. 28, 2015 (EP) .................................... 15182941

(51) Int. Cl.
*A61M 5/24* (2006.01)
*A61C 19/06* (2006.01)
(Continued)

(52) U.S. Cl.
CPC ......... *A61M 5/2466* (2013.01); *A61C 19/063* (2013.01); *A61D 7/00* (2013.01);
(Continued)

(58) Field of Classification Search
CPC .... A61M 5/2466; A61M 5/283; A61M 5/288; A61M 5/31571; A61M 5/31573; A61M 2005/247; A61M 5/24
See application file for complete search history.

(56) References Cited

U.S. PATENT DOCUMENTS 2,627,856 A    4/1951   Waterman
2,737,948 A *  3/1956   Brown .................. A61M 5/288
                                                    604/192
(Continued)

FOREIGN PATENT DOCUMENTS

CN    101715351 A    5/2010
EP      2905040 A1   8/2015
(Continued)

OTHER PUBLICATIONS

International Search Report dated Feb. 3, 2017 in corresponding International Application No. PCT/EP2016/069720, filed Aug. 19, 2016.
(Continued)

*Primary Examiner* — Tiffany Legette
(74) *Attorney, Agent, or Firm* — Global IP Counselors, LLP (57) ABSTRACT

A discharger for discharging a predetermined amount of fluid includes a housing defining a longitudinal first axis and having a proximal end and a distal end, a discharge section having a discharge passage for the fluid extending between an inlet opening and an outlet opening of the discharge section, a carriage cooperating with the proximal end region of the housing such that the carriage is moveable relative to the housing along the first axis, the carriage including a receiving space for the fluid, and a piercing tip having a flow channel for establishing a flow connection for the fluid from the receiving space to the inlet opening of the discharge section, the piercing tip defining a centrally extending longitudinal second axis and having a shell surface. The shell surface of the piercing tip has an essentially convexly curved.

19 Claims, 4 Drawing Sheets

(51) Int. Cl.
*A61M 5/28* (2006.01)
*A61M 5/315* (2006.01)
*A61D 7/00* (2006.01)

(52) U.S. Cl.
CPC ............ *A61M 5/24* (2013.01); *A61M 5/2429* (2013.01); *A61M 5/283* (2013.01); *A61M 5/288* (2013.01); *A61M 5/31571* (2013.01); *A61M 5/31573* (2013.01); *A61M 2005/247* (2013.01)

(56) References Cited

U.S. PATENT DOCUMENTS

| | | | |
|---|---|---|---|
| 3,570,486 A * | 3/1971 | Engelsher | B01F 13/002 604/88 |
| 3,931,815 A | 1/1976 | Takatsuki | |
| 5,354,537 A | 10/1994 | Moreno | |
| 2003/0088217 A1 * | 5/2003 | Bergeron | A61M 31/00 604/228 |
| 2008/0245314 A1 | 10/2008 | Brodowski et al. | |
| 2009/0292240 A1 * | 11/2009 | KraMer | A61M 5/31596 604/82 |
| 2013/0018311 A1 | 1/2013 | Denning et al. | |
| 2015/0027241 A1 | 1/2015 | Domkofski et al. | |
| 2015/0101595 A1 | 4/2015 | Hancock et al. | |

FOREIGN PATENT DOCUMENTS

| | | |
|---|---|---|
| JP | H08-155028 A | 6/1996 |
| JP | 2002-172166 A | 6/2002 |
| WO | 00/13723 A2 | 3/2000 |
| WO | 2012166801 A1 | 12/2012 |
| WO | 2015/124172 A1 | 8/2015 |

OTHER PUBLICATIONS

International Preliminary Report on Patentability and Written Opinion dated Mar. 6, 2018 in corresponding International Application No. PCT/EP2016/069720, filed Aug. 19, 2016.

Japanese Office Action dated Jun. 23, 2020 in corresponding JP Patent Application No. 2018-510979 (with English Translation).

* cited by examiner

Fig.10

DISCHARGER WITH IMPROVED PIERCING TIP

CROSS-REFERENCE TO RELATED APPLICATION

This application is a U.S. National Stage application of International Application No. PCT/EP2016/069720, filed Aug. 19, 2016, which claims priority to European Application No. 15182941.3, filed Aug. 28, 2015, the contents of each of which are hereby incorporated herein by reference.

BACKGROUND

Field of the Invention

The present disclosure relates to a discharger for discharging a predetermined amount of fluid and to a discharge system comprising the discharger. The present disclosure further relates to the use of the discharger and the discharge system for discharging a fluid including at least one medical, dental or veterinary agent.

Background of the Invention

Dischargers such as expendable syringes for use in the medical, dental or veterinary field are generally known which comprise one or more compartments in which the medical, dental or veterinary agent or a liquid including the medical, dental or veterinary agent is contained before use. The compartments are normally sealed with various kinds of barrier foils in order to isolate its contents from the environment.

EP 2 905 040 A1 describes a discharger for discharging a predetermined amount of fluid having a carriage comprising a receiving space for the fluid and a piercing tip for piercing a sealing foil of the receiving space, with the shell surface of the piercing having a concavely curved configuration.

US 2015/0101595 A1 and WO 2012/166801 A1 disclose discharge devices comprising a blister dosage form containing the fluid to be discharged as well as an internal piercing nozzle. By moving a plunger against the blister dosage form the internal piercing nozzle is pushed against the inner surface of a sealing foil of the blister dosage form and the fluid is forced through inlet ports disposed at the bottom of the piercing nozzle through an internal channel to finally leave the piercing nozzle at its tip in spray form.

SUMMARY

In general, before discharging the content of such a compartment the foil must be pierced by a plunger, spike or tip of suitable shape and hardness. Depending on the type of discharger also a flow connection between the compartment and a hollow spike or tip needs to be established, where appropriate. It is, on the one hand, important that the foil gets reliably pierced and, on the other hand, that the hollow spike or tip does not become clogged by a small piece of the foil. Furthermore, it is important that the force which needs to be applied for initially piercing or puncturing the foil is appropriate for the user. A problem often encountered with known applicators is a permanent change of the force which has to be applied during the discharging process, in particular after the foil has been pierced. Such force variations, in general, make a uniform discharge of the respective contents extremely difficult for the user, particularly because the contents often are present in only very small quantities.

Another issue that enhances this problem is a great variety of available barrier foils with highly diverse characteristics, especially in terms of elasticity and brittleness.

In view of the foregoing, it is an object of the present invention to provide a discharger which enables a reliable piercing of a wide variety of available barrier foils. At the same time the discharger should enable a mostly continuous and complete discharge of a predetermined amount of fluid, thereby improving its ease of handling.

These objects are satisfied by a discharger having the features described herein.

In accordance with an embodiment of the invention a discharger for discharging a predetermined amount of fluid comprises a housing defining a longitudinal first axis and having a proximal end and a distal end, a discharge section having a discharge passage for the fluid extending between an inlet opening and an outlet opening of the discharge section, a carriage cooperating with the proximal end region of the housing such that the carriage is moveable relative to the housing along the first axis, the carriage comprising a receiving space for the fluid, and a piercing tip being separate from the carriage and having a flow channel for establishing a flow connection for the fluid from the receiving space of the carriage to the inlet opening of the discharge section, the piercing tip defining a centrally extending longitudinal second axis and having a shell surface, wherein the shell surface of the piercing tip has an essentially convexly curved, in particular dome-shaped, configuration.

The discharger, in general, may be adapted to be used in the medical, dental or veterinary field or in the health care sector. The fluid to be discharged is in particular a liquid which includes at least one medical, dental or veterinary agent. The present disclosure is, however, not limited to the medical, dental or veterinary sector and can be used in other appliances in which it is desirable to discharge a predetermined amount of fluid in a reliable and uniform manner.

The present disclosure is not limited to the discharge of fluids such as liquids. Rather, the discharger as disclosed herein may alternatively be adapted or used to discharge viscous or gel-like materials.

In a preferred embodiment, the flow channel is centrally located within the piercing tip and extends along the longitudinal second axis defined by the piercing tip, thereby establishing a flow connection to the inlet opening of the discharge section.

The flow channel may also be located at an offset position relative to the longitudinal second axis. In this case, the flow channel, for example, may extend inclined relative to the second axis. The flow channel may also be divided into different axially and radially extending portions. For example, the flow channel may be divided into a first axial portion extending offset from the second axis merging into a radial portion which, in turn, merges into a second axial portion extending offset from the second axis or along the second axis, thereby establishing a flow connection to the inlet opening.

The flow channel may be cylindrical and preferably has a diameter between $1/5$ and $1/20$, more preferably between $1/7$ and $1/15$, particularly between $1/9$ and $1/11$ of a diameter of the piercing tip at its widest point. This widest point, in general, corresponds to the point where the piercing tip starts to taper. However, the flow channel may also have an oval, triangular or rectangular cross-section, for instance.

The flow channel defines an aperture at the shell surface of the piercing tip, i.e. the aperture represents an interruption of the shell surface. Unless otherwise stated, this aperture shall—within the scope of the following discussion of the configuration or shape of the piercing tip—not be considered in detail. This means, the discussion, in general, shall be based on a notional closed shell surface of the piercing tip, unless otherwise stated.

According to the invention, an outer surface of the piercing tip is convexly curved or vaulted to the outside. In other words, the shell surface of the piercing tip contains at least an outer surface section which has a convexly curved configuration. This means that the piercing tip may also contain at least one surface section which is not convexly curved, but rather is, for example, conical or truncated conical. According to the invention, however, the shell surface of the piercing tip has an essentially convexly curved configuration. More preferably, the piercing tip has an essentially dome-shaped configuration. In this context, the expression "essentially" means that the main configuration of the piercing tip, i.e. the main part of the shell surface of the piercing tip, is convexly curved or dome-shaped, respectively, but that there may be small regions, in particular in an area where the aperture of the flow channel is located, in which the configuration may slightly deviate from a convexly curved or dome-shaped configuration. It is of course also possible that the shell surface of the piercing tip has a complete convexly curved or dome-shaped configuration.

In a preferred embodiment, the piercing tip is essentially rotationally symmetric about the centrally extending longitudinal second axis defined by the piercing tip. It is particularly preferred in this context that the longitudinal second axis corresponds to the longitudinal first axis defined by the housing of the discharger, i.e. the piercing tip is preferably also essentially rotationally symmetric about the longitudinal first axis. Against this background, the expression "essentially" also implies that the piercing tip, in particular in an area where the aperture of the flow channel is located, may slightly deviate from a rotationally symmetric configuration.

Surprisingly, it turned out that a piercing tip having a convexly curved outer surface, in particular being essentially rotationally symmetric, is especially well-suited not only for reliably piercing a wide variety of barrier foils but also for a continuous and uniform discharge process. The reason for this is that the piercing tip according to the invention combines two features. On the one hand, only a relative moderate and user-friendly piercing force is necessary to initially pierce the foil. On the other hand, in particular due to its convexly curved configuration, the force that must be applied during the displacement of the piercing tip, i.e. during the discharge process, remains essentially constant over a wide distance. This ensures a highly homogeneous discharge, as the user during the discharge process only needs to apply a substantially constant and moderate force.

The shape of the piercing tip being essentially rotational symmetrical can be defined by two surface lines of a longitudinal cross-section along the second axis. The point at which the two surface lines intersect may be referred to as apex or vertex of the piercing tip.

In embodiments having a piercing tip being essentially rotationally symmetric, the two surface lines are essentially axially symmetric relating to the longitudinal second axis. In this case, the configuration of the two surface lines is essentially independent of the relative position of the longitudinal cross-section along the second axis. This means that two surface lines resulting from a first longitudinal cross-section along the second axis essentially have the same configuration as two surface lines resulting from a second longitudinal cross-section along the second axis being rotated, for example, by 90° relative to the first longitudinal cross-section. As above, the expression "essentially" implies that the surface lines, in particular in an area where the aperture of the flow channel is located, may slightly deviate from an axially symmetric configuration.

In embodiments having a flow channel being centrally located along the longitudinal second axis, the apex of the piercing tip can be an imaginary point located where the two surface lines would intersect if they were not interrupted by the flow channel.

Each of the two surface lines, in general, can be divided into two or more different sections having different characteristics. For example, a surface line can be divided into a linear section and a curved section, wherein the curved section may be a segment of a circle, an ellipse or a parable. The curved section of the surface line corresponds to the convexly curved outer surface section of the piercing tip. According to another example, a surface line can be divided into a section being a segment of a circle and a section being a segment of a parable or ellipse. According to still another example, a surface line can be divided into different sections, wherein each section represents a segment of a circle with a different diameter.

In an embodiment, the two surface lines of a longitudinal cross-section along the second axis intersect at an angle of between 70° and 110°, preferably between 80° and 100°, more preferably between 85° and 95°, in particular approximately 90°.

According to this embodiment, each of the two surface lines can be divided into at least two different sections. A linear section forming the apex of the piercing tip and at least another curved section representing a convexly curved outer surface section of the piercing tip. This means that the outer surface section of the piecing tip is divided into a conical section forming the apex and into at least another convexly curved surface section. Preferably, the conical section is rather small compared to the convexly curved surface section.

In a further embodiment, the shape of the piercing tip in a longitudinal cross-section along the second axis is defined by two surface lines, each surface line having at least one section defined by a curvature radius being larger than the diameter of the piercing tip at its widest point. According to this embodiment, each of the two surface lines comprises at least one section being a segment of a circle with a radius being larger than the diameter of the piercing tip at its widest point.

Expediently, this section represents the largest portion of the surface line, wherein it is particularly preferred that the surface line comprises only one further section, preferably having a curvature radius of smaller diameter.

The curvature radius being larger than the diameter of the piercing tip at its widest point may have a length of between 1.01 and 1.50, preferably between 1.05 and 1.40, more preferably between 1.10 and 1.30, in particular approximately 1.20, times the diameter of the piercing tip at its widest point.

In still a further embodiment, the piercing tip in a longitudinal cross-section along the second axis is defined by two surface lines, each surface line having at least two sections of different curvature radii. According to this embodiment, each of the two surface lines comprises at least two sections each being a segment of a circle with different radius.

Preferably, the curvature radius of the first section, i.e. the section which starts where the piercing tip begins to taper, is smaller than the curvature radius of the second section, i.e. the section which follows the first section. The length of the curvature radius of the first section lies preferably in the range between one tenth and half of the curvature radius of the second section.

The piercing tip according to another embodiment of the discharger may comprise a ridge at its apex, wherein the ridge preferably is perpendicular to the longitudinal second axis. The ridge, however, can also be inclined or slanted relative to the longitudinal second axis.

The length of the ridge preferably lies between 0.05 and 0.40, preferably between 0.10 and 0.35, more preferably between 0.15 and 0.30, times the diameter of the piercing tip at its widest point.

Even without taking into account the flow channel, the shape of the piercing tip having a ridge at its apex at least slightly deviates from a rotationally symmetric configuration. This, in particular, becomes obvious when considering a first longitudinal cross-section along the second axis and along the ridge as well as a second longitudinal cross-section being rotated by 90° relative to the first longitudinal cross-section.

With regard to the characteristics of the surface lines defining the piercing tip in the first cross-section, largely the same applies as outlined above relating to the essentially rotational symmetrical embodiments. However, instead of an apex, the piercing tip has a ridge-like elevation which preferably is located above an imaginary apex of the piercing tip. This imaginary apex is located where the two surface lines would intersect if they were not interrupted by the ridge.

With regard to the second longitudinal cross-section being rotated by 90° relative to the first one, i.e. the plane of the second cross-section is perpendicular to the ridge, the shape of the piercing tip preferably can be described by two surface lines intersecting at an angle of between 70° and 110°, preferably between 80° and 100°, more preferably between 85° and 95°, in particular approximately 90°. This means that each of the two surface lines is divided into a linear section corresponding to a lateral edge of the ridge and at least one curved section which may have the characteristics as outlined previously.

Expediently, the ridge is interrupted by the flow channel such that two protrusions adjacent to the flow channel are formed. In other words, the flow channel divides the ridge into two separated ridge-like protrusions which preferably have about the same dimensions.

Advantageously, these protrusions lower the piercing force that has to be initially applied for puncturing a barrier foil. In this way, a wide variety of barrier foils can be reliably punctured and the discharger according to the present invention can be applied substantially independent of the type of barrier foil being used.

Expediently, the ridge or the protrusions adjacent to the flow channel are deformable, particularly upon being pressed against a counterpart, wherein the counterpart preferably represents an end section of the receiving space. Due to their deformability the protrusions are compressed when the piercing tip is forced towards the counterpart. In this way, the space between the piercing tip and the counterpart being available for the fluid to be discharged is minimized which, in turn, leads to lower amounts of fluid residues at the end of the discharge process. The compression of the protrusions progresses in such a way that the flow channel does not become clogged by the displaced material which is basically due to the position and shape of the protrusions.

The piercing tip is preferably at least partially positioned inside the housing so as to protrude into the receiving space of the carriage when the carriage is being moved towards the distal end of the housing. By means of the flow channel, the piercing tip thereby establishes a flow connection for the fluid to the inlet opening of the discharge section.

By providing a carriage with a receiving space for the fluid, either a separate container adapted to be loaded into the receiving space and containing the predetermined amount of fluid can be loaded into the carriage or the predetermined amount of fluid to be discharged can be directly stored inside the receiving space. The amount of the fluid either contained in the container or in the carriage itself may for example range between 0.1 and 10 ml, preferably between 0.5 and 5 ml.

Expediently, the fluid inside the receiving space or container is protected from environmental influences by a breakable seal, in particular a barrier foil.

It is preferred that a separate container is applied to avoid a direct storage of the fluid inside the receiving space of the carriage. The carriage, in this way, can be reusable since it normally does not come into contact with the fluid to be discharged. Even if the carriage or the whole discharger is a disposable product by providing a separate container containing the fluid storage costs for the discharger can be reduced since the discharger and the containers can be stored independently.

In a preferred embodiment, an inner contour of the receiving space or an inner contour of the container is essentially complementary in shape to the piercing tip. The expression "essentially", in this context, implies that the shape of the inner contour can deviate from an exact complementary shape of the piercing tip in an area where the aperture of the flow channel is located and, where applicable, in an area where the protrusions are located.

This design allows for a nearly complete discharge of the fluid since the space available for the fluid can be completely filled by the piercing tip resulting in a nearly complete displacement of the fluid.

In this context, the piercing tip being essentially rotationally symmetric is of particular advantage since a special orientation of the piecing tip relative to the complementary shaped and accordingly also rotationally symmetric inner contour of the receiving space or the container is not necessary to establish a form-fitting connection. This also facilitates the assembly of the discharger since neither the piercing tip nor the complementary designed receiving space or container needs to adopt a preferred orientation direction.

It should be noted in this connection that also the piercing tip comprising two deformable protrusions can establish a form-fitting connection to the inner contour of the receiving space or the container even if this inner contour is rotationally symmetric and has not been specially adapted to the protrusions. Due to the deformability of the protrusions the piercing tip comprising the deformable protrusions is able to adapt to the rotationally symmetric inner contour of the receiving space or the container upon applying a force.

In this way the advantage of a reduced initial force for puncturing a barrier foil being due to the protrusions at the piercing tip and the advantage of a nearly residue-free discharge can be combined.

In a further embodiment the piercing tip is formed integrally with the housing and/or the discharge section. In other words, it is preferable that the piercing tip and the housing and/or the discharge section are formed in one piece.

However, it can also be preferable when the piercing tip is formed as a unitary separate piece which, for example, can be linked to the housing and/or the discharge section for example by a plug connection.

Expediently, the piercing tip is formed by injection molding and preferably includes an elastically deformable polymer selected from the group comprising polypropylene, cyclic olefin polymer, polyethylene, polyamide, polybutylenerephthalat and polymethyl methacrylat.

The discharger and/or the container, in general, may be fabricated from any suitable material. In one embodiment, the material is plastic, wherein the same polymers as named above are suitable. Alternatively, the material may be glass, metal or an alloy.

In an embodiment, the discharger further comprises a securing means or device which is adapted to prevent the carriage from being unintentionally moved from a starting position along the longitudinal first axis. This securing device facilitates the handling of the discharger by avoiding unintentional operation of the carriage.

In particular, the securing device may comprise a pin/slot arrangement having at least one pin formed at the carriage and at least one slot formed in a wall of the housing. The pin is guided by the slot. The slot may comprise a first portion extending in a circumferential direction and merging into an axial slot portion extending along the longitudinal first axis of the discharger. Such securing device requires the user to rotate the carriage with respect to the housing before the carriage can be pushed into the housing and towards a final discharge position.

A means or devices such as wing-like projections can be formed at an outer side of the housing so that the discharger may be used like a common syringe by holding the discharger with one finger at each projection and with the thumb on a proximal end of the carriage or of a container loaded into the carriage, thereby providing for a comfortable single-hand operation of the discharger.

Another aspect of the invention relates to a discharge system comprising a discharger as disclosed herein and at least one container holding an amount of fluid to be discharged, wherein the container is adapted to be loaded into the receiving space of the carriage of the discharger.

A further aspect of the invention relates to the use of a discharger as disclosed herein or of a discharge system as disclosed herein, for discharging a liquid including at least one medical, dental or veterinary agent, wherein in particular the amount of the liquid lies in the range of 0.1 to 10 ml, preferably between in the range of 0.5 to 5 ml.

With respect to one common classification applied in the medical, dental or veterinary field or the health care sector, the discharger and the discharge system as provided by the present disclosure belong to the group consisting of systems without protection cap.

BRIEF DESCRIPTION OF THE DRAWINGS

The invention will be explained in more detail hereinafter with reference to the drawings.

DETAILED DESCRIPTION

In the following the same reference numerals will be used for parts having the same or equivalent function. Any statements made having regard to the direction of a component are made relative to the position shown in the drawing and can naturally vary in the actual position of application.

Figures 1, 2, 3:
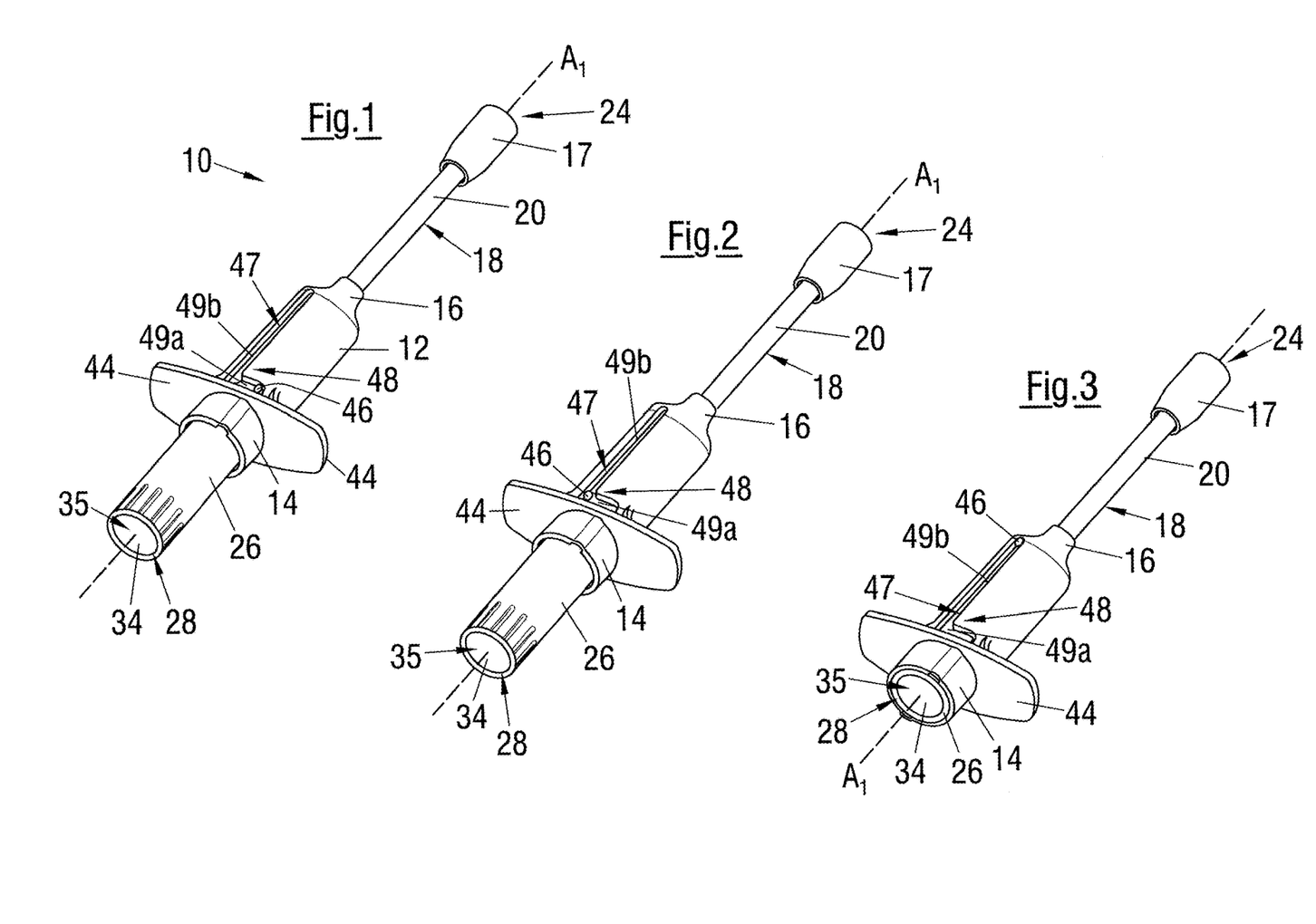
FIGS. 1 to 3 show a discharge system comprising a discharger according to the present disclosure in different states of use.

FIG. 1 shows a discharger 10 comprising a housing 12, a carriage 26 and a discharge section 18. The housing 12 defines a longitudinal first axis $A_1$ and includes opposing wing-like protrusions 44 similar to a common disposable syringe. The carriage 26 is received in a proximal end region 14 of the housing 12. The carriage 26 defines a receiving space 28 into which a container 34 has been loaded through an opening 35 of the carriage 26. The discharger 10 and the container 34 form a discharge system and are generally designed as disposable articles intended for one-time use only.

The discharge section 18 of the discharger 10 comprises a discharge passage 20 and extends from within the housing 12 through a tapered distal end 16 towards a thickened distal end portion 17. The distal end portion 17 can be formed integrally with the discharge passage 20 or can be made as a separate component connected in a suitable manner to the discharge passage 20. The distal end portion 17 moreover defines an outlet opening 24.

The distal end portion 17, in general, can be adapted to the type and site of application and can be in the form of or comprise a spray head, a needle (cannula), a brush, a sponge or a pipette. For large area applications, for example, a spray head or a sponge can be of advantage, whereas selective applications might require a needle or a plain tube of small diameters.

The discharger 10 has a securing means or device 48 comprising a slot 47 being formed in the housing 12 and cooperating with a pin 46 being formed at the carriage 26. The slot 47 is divided into a circumferential portion 49a and into a longitudinal portion 49b extending in parallel to the first axis $A_1$.

The discharger 10 in FIG. 1 is shown in an initial state of use with the pin 46 being situated at the end of the circumferential portion 49a of the slot 47. In this initial state of use a movement of the carriage 26 along the longitudinal axis $A_1$ towards the distal end 16 is prevented.

FIG. 2 shows the discharger 10 in a starting position with the pin 46 being situated at the intersection point of the circumferential portion 49a and the longitudinal portion 49b of the slot 47. In this state the carriage 26 is movable along the longitudinal axis $A_1$ towards the distal end 16.

FIG. 3 shows the discharger 10 in a final discharge position with the pin 46 being situated at the end of the longitudinal portion 49b of the slot 47. In this state the carriage 26 is completely situated inside the housing 12.

Figures 4, 5:
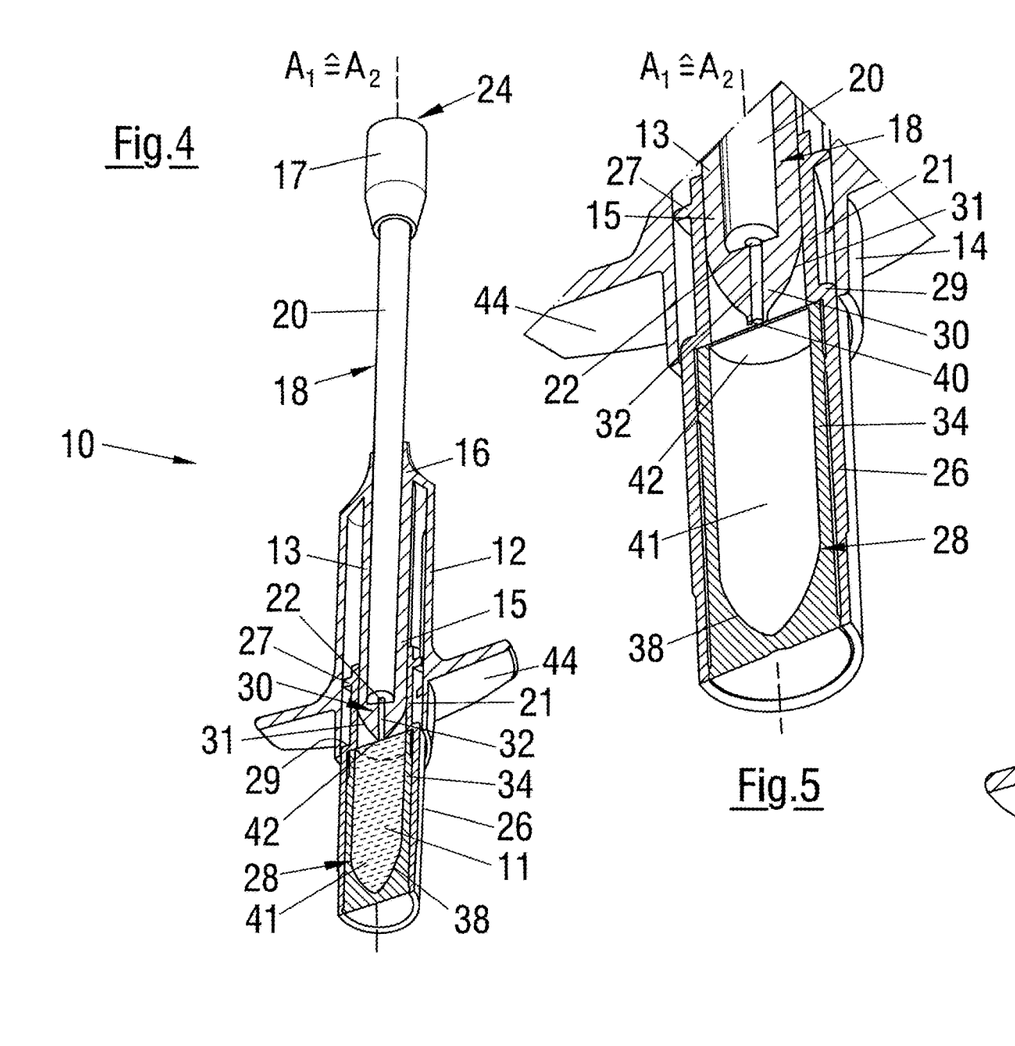
FIG. 4 shows a partial cross-section along the longitudinal first axis of the discharge system of FIG. 1.
FIG. 5 shows an enlarged portion of FIG. 4.

FIG. 4 shows the discharger 10 of FIG. 1 in a partial cross-section along the longitudinal first axis $A_1$. The discharge section 18, however, is not shown in cross-section.

FIG. 4 illustrates the container 34 located inside the receiving space 28 of the carriage 26. The container 34 is made as a capsule which has a cylindrical outer shape and is filled with a fluid 11 to be discharged. The fluid 11 inside the container 34 is located in a fluid reservoir 41 which is protected from the environment by a breakable seal 42 in the form of a foil. This is even more clear in the enlarged portion of FIG. 4 depicted in FIG. 5. The amount of the fluid 11 inside the fluid reservoir 41 is approximately 0.5 ml. A circumferential shoulder 29 of the carriage 26 acts as an axial stop for the container 34 when being loaded into the receiving space 28 of the carriage 26.

Moreover, FIG. 4 illustrates a sleeve portion 13 integrally formed with the housing 12. The discharge passage 20 is fitted into the sleeve portion 13. A proximal end portion 15 of the sleeve portion 13 is fitted into a distal cylindrical portion 21 of the carriage 26 through a distal opening thereof. The housing 12 generally has a cylindrical outer shape with a constant inner diameter. In order to conform the distal cylindrical portion 21, the outer diameter of which is smaller than the inner diameter of the housing 12, to the inner diameter of the housing 12, a flange 27 is formed integrally with the distal cylindrical portion 21.

The proximal end portion 15 of the sleeve portion 13 comprises a piercing tip 30 having a flow channel 32 being connected to an inlet opening 22 of the discharge passage 20. The piercing tip 30 is formed integrally with the sleeve portion 13 of the housing 12 and defines a centrally extending longitudinal second axis $A_2$ which in this embodiment corresponds to the first axis $A_1$.

From FIG. 5 it is apparent that the flow channel 32 extends along the longitudinal first or second axis $A_1$, $A_2$. Also the configuration of the piercing tip 30 is clear. The piercing tip 30 has a convexly curved outer surface 31 and moreover comprises two protrusions 40 adjacent to the flow channel 32, respectively. The protrusions originate from a ridge 39 that has been interrupted by the flow channel 32 during the manufacturing process (see FIG. 10).

FIG. 5 further reveals that the fluid reservoir 41 has a rotationally symmetric inner contour 38. Apart from the protrusions 40, the inner contour 38 is complementary to the outer shape of the piercing tip 30.

Figure 6:
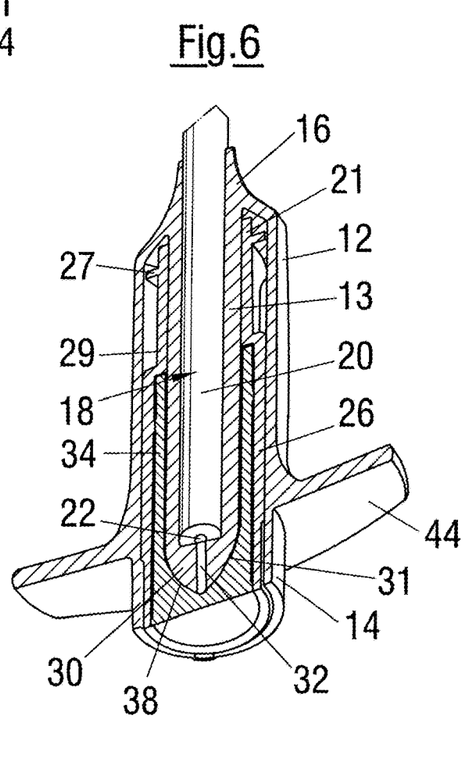
FIG. 6 shows a partial cross-section along the longitudinal first axis of a proximal portion of the discharge system of FIG. 3, FIGS. 7 to 9 respectively show a first cross-section of a piercing tip according to the present invention and a side view of the piercing after a rotation by 90°.

FIG. 6 shows the discharger 10 in its final discharge position, i.e. the carriage 26 has been fully moved towards the distal end 16 into the housing 12. In this position, the piercing tip 30 and at least the proximal end portion 15 of the sleeve portion 13 are located in the fluid reservoir 41 of the container 34. The seal 42 has been pierced and the fluid 11 has been displaced. The protrusions 40 have been compressed such that the piercing tip 30 and the inner contour 38 of the fluid reservoir 41 establish a form-fitting connection.

Figure 7:
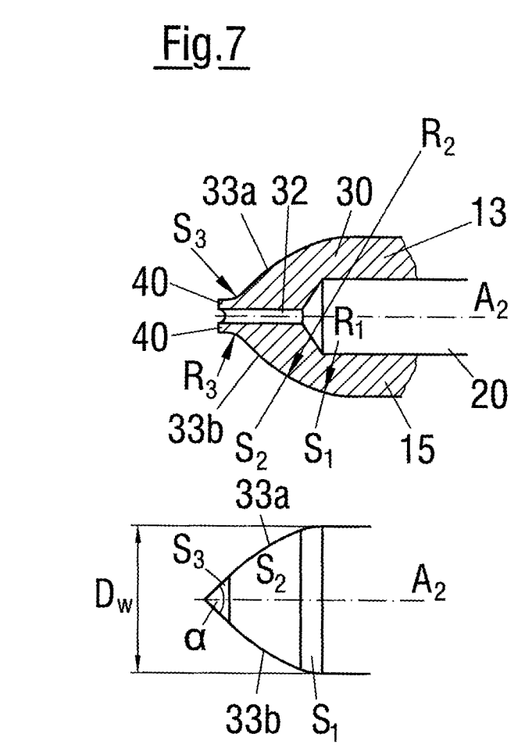

FIG. 7 shows detailed views of the piercing tip 30 of FIGS. 4 to 6. The upper pane contains a cross-sectional view along the longitudinal second axis $A_2$ and along the two protrusions 40. The two protrusions 40 are located adjacent to a proximal entry opening of the centrally located flow channel 32. The shape of the piercing tip 30 is defined by two surface lines 33a, 33b which are axially symmetric. Each surface line 33a, 33b consists of three sections $S_1$, $S_2$, $S_3$, wherein each section $S_1$, $S_2$, $S_3$ is defined by a curvature radius $R_1$, $R_2$, $R_3$. This means each section $S_1$, $S_2$, $S_3$ is a segment of a circle. The length of the curvature radii $R_1$, $R_2$, $R_3$ is indicated by respective arrows. The radius $R_1$ of the first section $S_1$ is roughly one fifth of the radius $R_2$ of the second section $S_2$. The length of the radius $R_2$ of the second section $S_2$ is more than half the length of a diameter $D_W$ of the piercing tip 30 at its widest point (see lower pane). The third section $S_3$ particularly defines the shape of the protrusions 40. The length of the corresponding radius $R_3$ is approximately half of the radius $R_1$. Thus, the convex shape of the piercing tip 30 is mainly defined by sections $S_1$ and $S_2$.

The lower pane of FIG. 7 shows a side view of the piercing tip 30 shown in the upper pane after a rotation by 90°. The sections $S_1$, $S_2$, $S_3$ are indicated by lines perpendicular to the second axis $A_2$. It is clearly visible that the surface lines defining section $S_3$ in this view run linear and intersect at an angle α of approximately 90°. Thus, the protrusions 40 in this view have a triangular profile.

Figure 10:
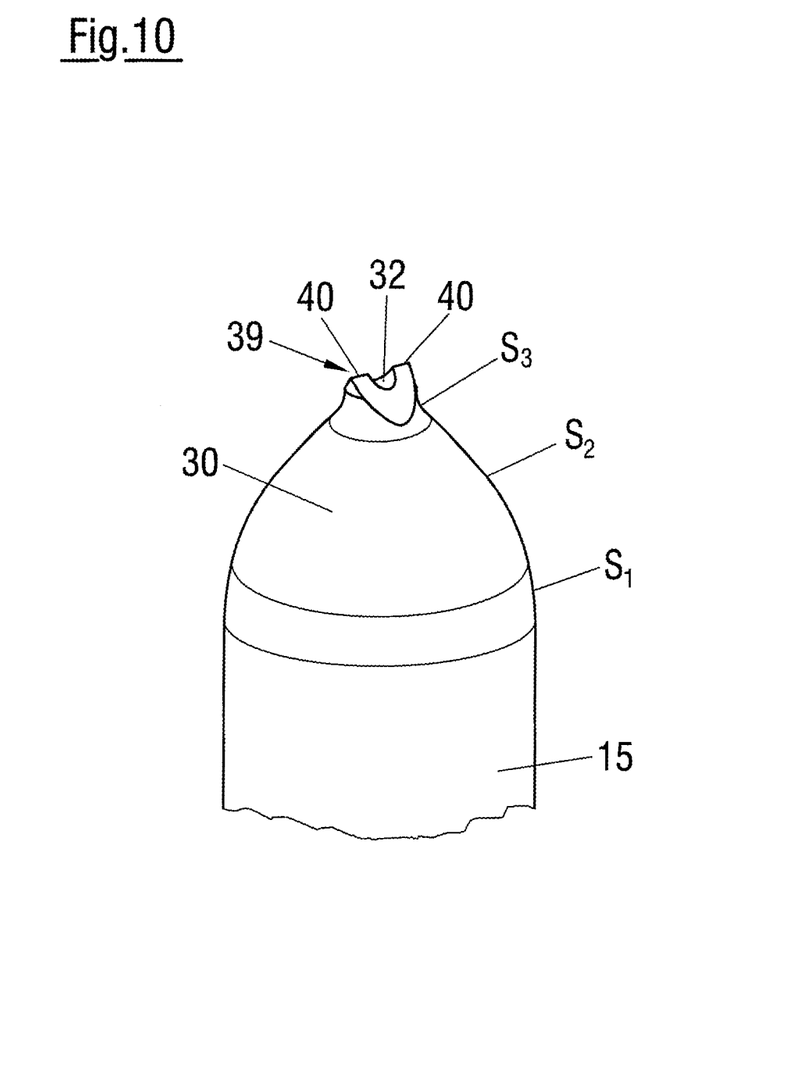
FIG. 10 shows a perspective view of a piercing tip having a ridge.

A perspective view clearly indicating the convex shape of the outer surface of the piecing tip 30 according to FIGS. 4 to 7 is also shown in FIG. 10.

Figure 8:
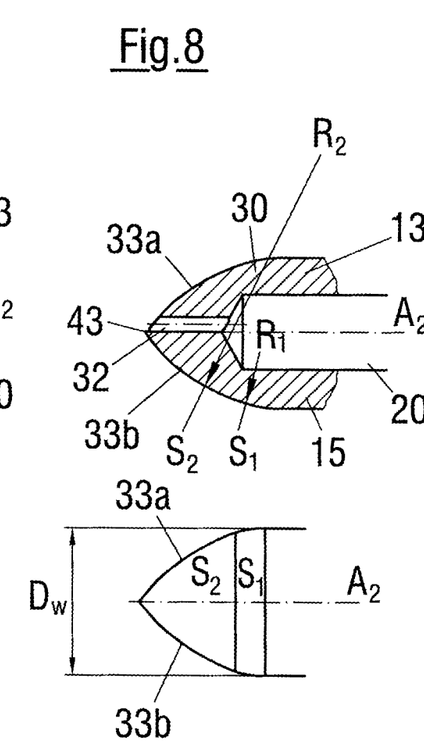

FIG. 8 in its upper pane shows a cross-section along the longitudinal second axis $A_2$ of another embodiment of the piercing tip 30 according to the present invention. Each surface line 33a, 33b consists of two sections $S_1$, $S_2$ each being a segment of a circle having a corresponding radius $R_1$, $R_2$. Regarding the length of the radii $R_1$, $R_2$ the same applies as for FIG. 7.

The flow channel 32 is not centrally located within the piercing tip 30 but is located at an offset position relative to the second axis $A_2$. This means the piercing tip 30 slightly deviates from a rotationally symmetric configuration. Due to this arrangement the piercing tip 30 comprises a thorn-like protrusion 43 which, however, in the side view after a rotation by 90° depicted in the lower pane of FIG. 7 is not visible anymore. It turned out that this configuration lowers the piercing force that has to be initially applied for puncturing the seal 42, however, not to the same extend as for the embodiment comprising two protrusions 40.

Figure 9:
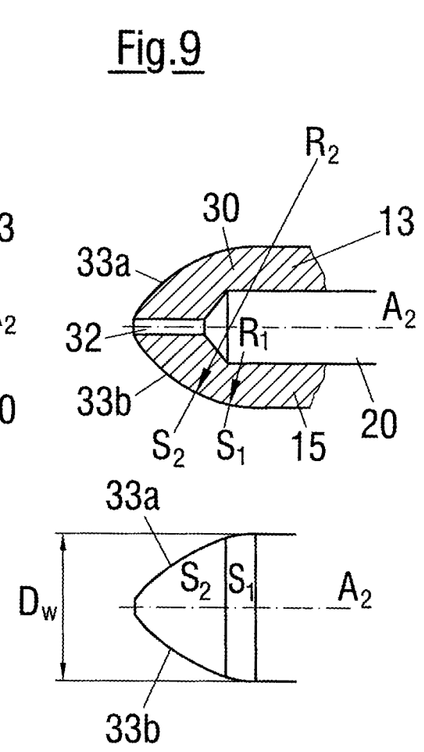

FIG. 9 in its upper pane shows a cross-section along the longitudinal second axis $A_2$ of a further embodiment of the piercing tip 30 according to the present invention. The piercing tip 30 is rotationally symmetric about the second axis $A_2$ since the flow channel 32 is centrally located within the piercing tip 30. Each surface line 33a, 33b consists of two sections $S_1$, $S_2$ each being a segment of a circle having a corresponding radius $R_1$, $R_2$. Regarding the length of the radii $R_1$, $R_2$ the same applies as for FIGS. 7 and 8.

Both representations, the cross-section in the upper pane of FIG. 9 and the side view after a rotation by 90° in the lower pane, indicate that the piercing tip 30 is slightly cut due to the arrangement of the flow channel 32. Thus, the apex of the piercing tip 30 is an imaginary point located where the two surface lines 33a, 33b would intersect if they were not interrupted by the flow channel 32.

Any of the three piercing tips according to FIGS. 7 to 8 are able to initially punctuate a foil with a moderate and user-friendly piercing force, wherein the piercing tip comprising two protrusions 40 has shown the best results in this regard. The convexly curved configuration, however, is mainly responsible that the force which needs to be applied during the movement or displacement of the piercing tip remains essentially constant over a wide distance. This constant force distribution was shown by all of the three piercing tips according to FIGS. 7 to 9 and can therefore be regarded as independent of the shape in the rather small region of the apex of the piercing tip. With particular benefit it is therefore possible to ensure a highly homogeneous discharge by merely adapting the shape in the apex region of the piercing tip to the characteristics of the applied foil.

For operating the discharger 10, i.e. to discharge the fluid 11 inside the container 34 through the discharge passage 20 out of the outlet opening 24, the carriage 26 including the container 34 needs to be pushed towards the distal end 16 into the housing 12. However, the securing device 48 prevents the carriage 26 from being unintentionally pushed into the housing 12 when the discharger is in an initial state of use. In this initial state of use shown in FIGS. 1, 4 and 5, the piercing tip 30 is still positioned spaced apart from the seal 42 of the container 34, i.e. the piercing tip 30 does not yet protrude into the fluid reservoir 41 of the container 34.

In order to discharge the fluid 11, the user, firstly, has to deliberately rotate the carriage 26 counter-clockwise with respect to the housing 12 until the pin 46 is aligned with the axial portion 49b of the slot 47. For facilitating the rotation of the carriage 26, the outer surface of the carriage 26 may be roughened or provided with longitudinal grooves providing a non-slip surface.

The carriage 26 now being in the starting position is movable along the longitudinal axis $A_1$. From the starting position the carriage 26 and the container 34 together can be actuated like a push button which can be pressed by the user with a thumb while counteracting this actuation by holding the housing 12 with two fingers behind the projections 44. Thus, to discharge the fluid 11 the user, secondly, has to deliberately push the carriage 26 towards the distal end 16. While the carriage 26 moves towards the distal end 16, the piercing tip 30 initially punctuates and then pierces the seal 42. The piercing tip 30 enters into the fluid reservoir 41 of the container 34, thereby urging the fluid 11 out of the container 34 through the flow channel 32 being connected to the discharge passage 20. The complementary shapes of the piercing tip 30 and the inner contour 38 of the fluid reservoir 41 ensure that essentially no residual amounts of fluid 11 remain within the container 34.

Since in many countries pertinent regulations prohibit a simple throwing away of medical, dental or veterinary substances, the lack of substantial residual amounts of fluid as provided by the discharge system as described herein simplifies the disposal of used containers and dischargers in accordance with the respective national regulations.

The invention claimed is:

1. A discharger for discharging a predetermined amount of fluid, comprising: a housing defining a longitudinal first axis and having a proximal end and a distal end; a discharge section having a discharge passage for the fluid extending between an inlet opening and an outlet opening of the discharge section; a carriage including a reservoir disposed therein, the reservoir configured to have the fluid disposed therein, the carriage cooperating with the proximal end of the housing such that the carriage is moveable relative to the housing along the longitudinal first axis to expel the fluid from the reservoir; and a piercing tip having a flow channel configured to establish a flow connection for the fluid from the reservoir to the inlet opening of the discharge section, the piercing tip defining a centrally extending longitudinal second axis and having a shell surface, the piercing tip being monolithic with the housing, and the shell surface of the piercing tip having convexly curved configuration, and the housing surrounding a proximal end of the discharge section and a distal end of the carriage.

2. The discharger according to claim 1, wherein the flow channel is centrally located within the piercing tip and extends along the centrally extending longitudinal second axis or the flow channel is located at an offset position relative to the centrally extending longitudinal second axis.

3. The discharger according to claim 1, wherein the piercing tip is rotationally symmetric about the centrally extending longitudinal second axis.

4. The discharger according to claim 1, wherein the piercing tip has a shape in a longitudinal cross-section along the centrally extending longitudinal second axis defined by two surface lines intersecting at an angle of between 70° and 110°.

5. The discharger according to claim 1, wherein the piercing tip in a longitudinal cross-section along the centrally extending longitudinal second axis is defined by two surface lines, each surface line having at least two sections of different curvature radii.

6. The discharger according to claim 1, wherein the piercing tip is at least partially positioned inside the housing so as to protrude into the reservoir when the carriage is being moved towards the distal end of the housing.

7. The discharger according to claim 1, wherein an inner contour of the reservoir holding an amount of fluid is complementary in shape to the piercing tip.

8. The discharger according to claim 1, wherein the piercing tip has a shape in a longitudinal cross-section along the centrally extending longitudinal second axis defined by two surface lines intersecting at an angle of between 850 and 95°.

9. The discharger according to claim 1, wherein the piercing tip at an apex thereof comprises a ridge.

10. The discharger according to claim 9, wherein the ridge is perpendicular to the centrally extending longitudinal second axis.

11. A method of discharging the fluid, comprising: providing the discharger according to claim 1; and discharging the fluid, the fluid including at least one medical, dental or veterinary agent, the fluid being an amount between 0.1 to 10 ml.

12. The discharger according to claim 1, wherein the shell surface has a dome-shape.

13. A discharge system comprising: a discharger according to claim 1; and at least one container configured to hold the fluid to be discharged, the container configured to be loaded into a receiving space of the carriage of the discharger.

14. A method of discharging the fluid, comprising: providing the discharge system of claim 13; and discharging the fluid, the fluid including at least one medical, dental or veterinary agent, the fluid being an amount between 0.1 to 10 ml.

15. A discharger for discharging a fluid, comprising: the fluid, comprising: a housing defining a longitudinal first axis and having a proximal end and a distal end; a discharge section having a discharge passage for the fluid extending between an inlet opening and an outlet opening of the discharge section; a carriage cooperating with the proximal end region of the housing such that the carriage is moveable relative to the housing along the first axis, the carriage comprising a receiving space for the fluid; and a piercing tip having a flow channel configured to establish a flow connection for the fluid from the receiving space to the inlet opening of the discharge section, the piercing tip defining a centrally extending longitudinal second axis and having a shell surface, the shell surface of the piercing tip having convexly curved configuration, and the piercing tip having a shape in a longitudinal cross-section along the centrally extending longitudinal second axis defined by two surface lines, each surface line having at least one section defined by a curvature radius being larger than a diameter of the piercing tip at a widest point thereof.

16. The discharger according to claim 15, wherein the curvature radius has a length of between 1.01 and 1.50 times the diameter.

17. The discharger according to claim 15, wherein the curvature radius has a length of between 1.10 and 1.30 times the diameter.

18. A discharger for discharging a fluid, comprising: the fluid, comprising: a housing defining a longitudinal first axis and having a proximal end and a distal end; a discharge section having a discharge passage for the fluid extending between an inlet opening and an outlet opening of the discharge section; a carriage cooperating with the proximal end region of the housing such that the carriage is moveable relative to the housing along the first axis, the carriage comprising a receiving space for the fluid; and a piercing tip at an apex thereof comprising a ridge, and having a flow channel configured to establish a flow connection for the fluid from the receiving space to the inlet opening of the discharge section, the piercing tip defining a centrally extending longitudinal second axis and having a shell surface, the shell surface of the piercing tip having convexly curved configuration, and the ridge being interrupted by the flow channel such that two protrusions adjacent to the flow channel are formed.

19. A discharger for discharging a fluid, comprising: a housing defining a longitudinal first axis and having a proximal end and a distal end; a discharge section having a discharge passage for the fluid extending between an inlet opening and an outlet opening of the discharge section; a carriage cooperating with the proximal end region of the housing such that the carriage is moveable relative to the housing along the first axis, the carriage comprising a receiving space for the fluid; and a piercing tip at an apex thereof comprising a deformable ridge, and having a flow channel configured to establish a flow connection for the fluid from the receiving space to the inlet opening of the discharge section, the piercing tip defining a centrally extending longitudinal second axis and having a shell surface, and the shell surface of the piercing tip having convexly curved configuration.

* * * * *